United States Patent [19]
Umber et al.

[11] Patent Number: 5,893,851
[45] Date of Patent: Apr. 13, 1999

[54] MULTIPLE CHUCK RESECTING TOOL

[75] Inventors: Ray E. Umber, Arlington; Larry Dale Estes, North Richland Hills; Townesend R. Scantlebury, Arlington, all of Tex.

[73] Assignee: Midas Rex Pneumatic Tools, Inc., Fort Worth, Tex.

[*] Notice: This patent is subject to a terminal disclaimer.

[21] Appl. No.: 08/837,446

[22] Filed: Apr. 18, 1997

[51] Int. Cl.⁶ .............................................. A61B 17/56
[52] U.S. Cl. ........................ 606/80; 606/79; 279/75
[58] Field of Search ........................... 606/80, 79, 85, 606/104, 96, 86; 279/75, 74, 125

[56] References Cited

U.S. PATENT DOCUMENTS

| | | | |
|---|---|---|---|
| 3,975,032 | 8/1976 | Bent et al. | 606/104 |
| 4,736,742 | 4/1988 | Alexson et al. | 606/80 |
| 5,219,174 | 6/1993 | Zurbrugg et al. | 279/82 |
| 5,222,956 | 6/1993 | Waldron | 606/80 |
| 5,330,480 | 7/1994 | Meloul et al. | 606/80 |
| 5,490,683 | 2/1996 | Mickel et al. | 279/75 |
| 5,569,256 | 10/1996 | Vaughn et al. | 606/80 |

*Primary Examiner*—Guy V. Tucker

[57] ABSTRACT

A coupling device attaches to a surgical resecting instrument with a motorized shaft for rotating surgical implements. The device houses a primary shaft which can be directly attached to the motorized shaft, and a secondary shaft which can be attached to the primary shaft through a hexagonally-shaped drive attachment with a bore. The primary shaft has several apertures with balls that engage an annular recess in the shank of a first implement to restrict its axial movement. The primary shaft also has a torque shoulder for engaging a torque shoulder on the first implement. If the first implement is removed, the secondary shaft can be installed to receive a second implement with a diameter smaller than that of the first implement. The secondary shaft also has several apertures with balls that engage an annular recess in a second implement shaft to restrict axial movement. The secondary shaft has axially spaced apart torque shoulders for engaging a torque shoulder on the second implement.

14 Claims, 3 Drawing Sheets

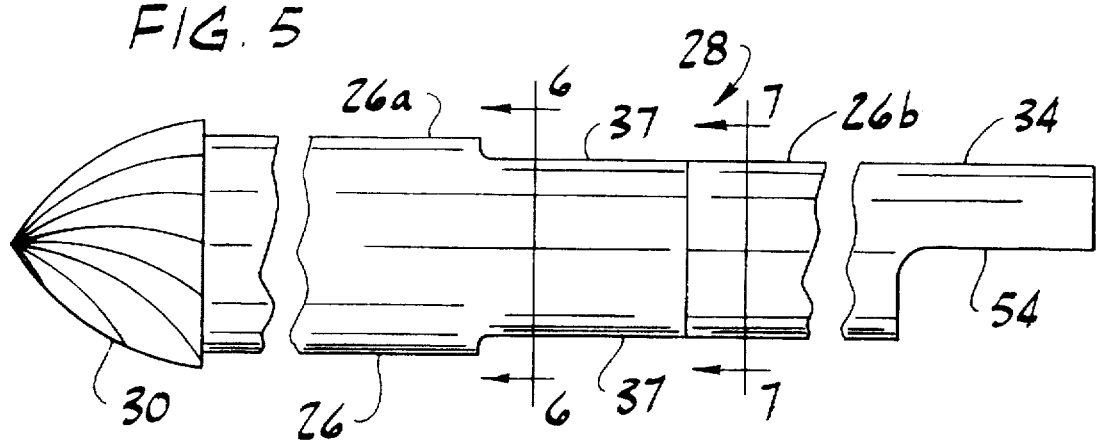
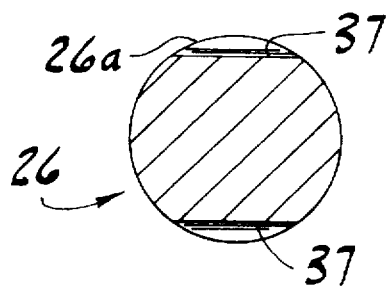
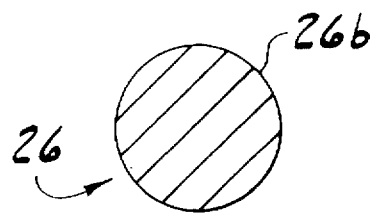
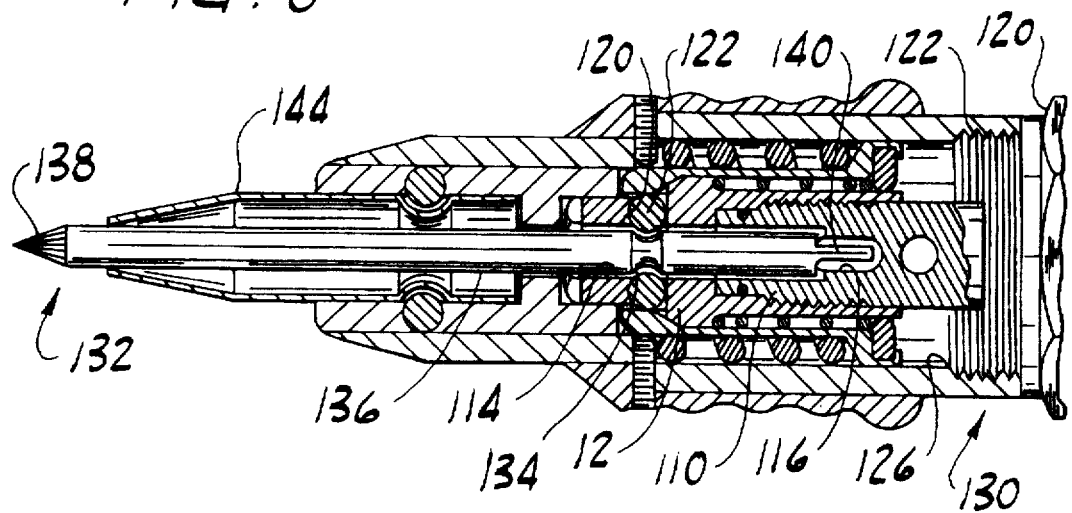

5,893,851

1

MULTIPLE CHUCK RESECTING TOOL

TECHNICAL FIELD

The present invention relates in general to surgical instruments for use in the dissection of bone and other tissue. In particular, the present invention relates to a coupling device for surgical instruments that is capable of driving surgical implements of different sizes.

BACKGROUND ART

Surgical instruments that utilize shafted implements driven by high speed motors for the dissection of bone and tissue are common in the art. These instruments are capable of driving implements of a specific diameter. However, not all implements have the same diameter. For example, some implements have a shank or shaft with a 1/8 inch diameter, while other implements have a shaft with a 3/32 inch diameter. When a surgeon needs to change to an implement with a diameter of a different size than he is currently using, he must use a different surgical instrument to do so. This procedure wastes time during surgery and adds unnecessary cost to the equipment needed. What is needed is a surgical instrument that is capable of handling implements of different sizes with relative ease.

DISCLOSURE OF INVENTION

A surgical instrument is used for the resection of bone and tissue. The instrument has a pneumatic motor that drives a primary shaft and spindle inside an attachment. Connected to the attachment is the base of a coupling which is threaded onto a neck of the attachment. The coupling receives a shafted tool implement which is used for cutting.

A support sleeve extends from the end of the coupling to support the implement. At one end of the implement is a cutting element. The implement has a shank diameter of 1/8 inch on its forward end. The rearward end has a 3/32 inch diameter and is separated from the forward end by two flats or shoulders. A tang extends from the end opposite of the cutting element. The shoulder on the tang may be used to apply torque to the implement.

The instrument comprises a secondary or tubular shaft that attaches to an intermediate member or boss which receives the spindle. The boss has a socket for receiving the tang of the implement. The tubular shaft is essentially cylindrical with a central bore that contains a shoulder. On the end opposite of the boss are two more shoulders. Any of these shoulders can engage a shoulder on the implement. The tubular shaft has a plurality of apertures with balls that engage an annular recess in the implement shank to limit axial movement. The instrument has another set of apertures and balls on its forward end for engaging a recess on the implement sleeve in the same way described for the implement shank.

The invention also has a primary shaft with a bore for receiving a larger diameter tool. The primary shaft can be accessed by removing the tubular shaft and the intermediate member. The primary shaft has a set of apertures and balls on its forward end for engaging a recess on the larger diameter tool in the same way described for the implement shank and the tubular shaft.

BRIEF DESCRIPTION OF DRAWINGS

FIG. 5 is an enlarged partial side view of the tool implement.

FIG. 6 is an enlarged cross-sectional view of the tool implement of FIG. 5 taken along the line 6—6.

FIG. 7 is an enlarged cross-sectional view of the tool implement of FIG. 5 taken along the line 7—7.

FIG. 8 is an enlarged cross-sectional view of the tool in a second mode constructed in accordance with the invention.

BEST MODE FOR CARRYING OUT THE INVENTION

Figure 1:
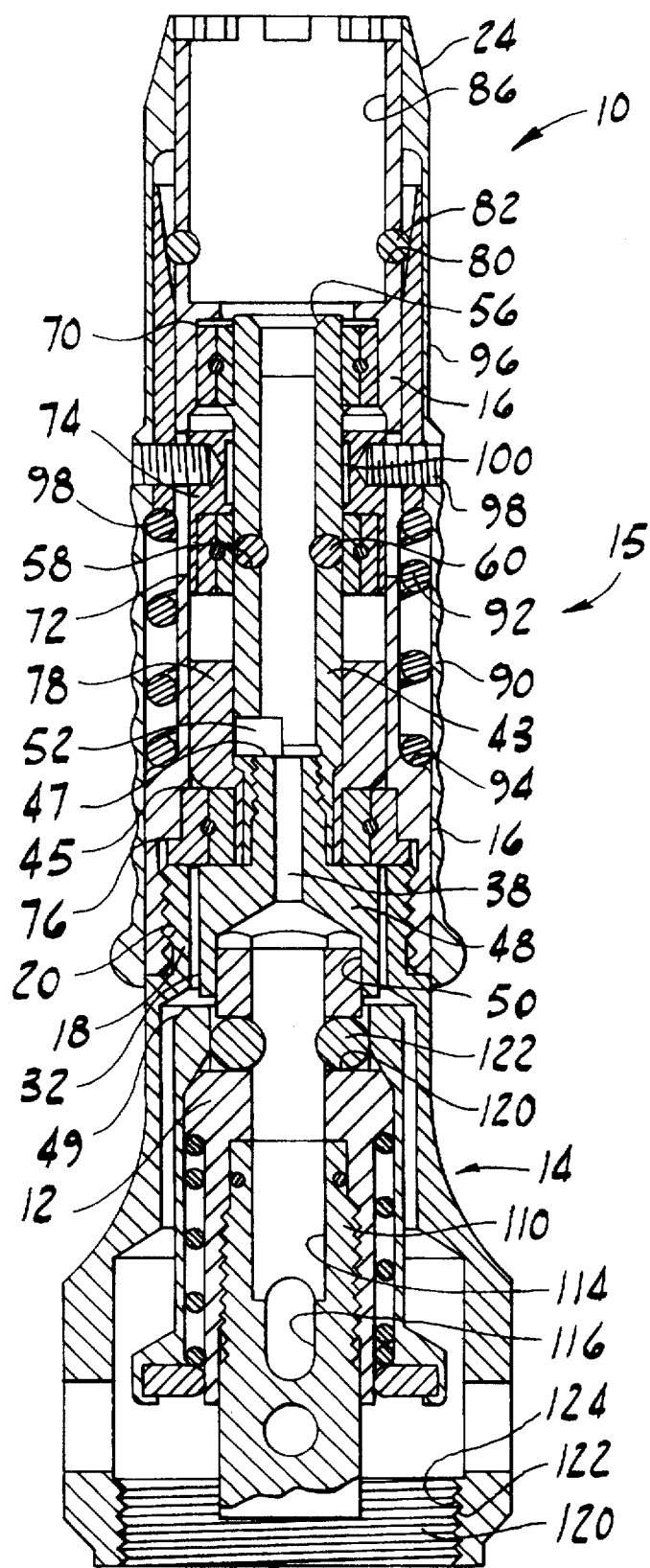
FIG. 1 is an enlarged cross-sectional view of the surgical instrument without the implement or sleeve installed and is constructed in accordance with the invention.

Referring to FIG. 1 showing a first mode, a surgical instrument 10 used for the resection of tissue in surgical procedures is shown. Instrument 10 is provided with a fluid driven motor (not shown) having an air conduit (not shown) which provides a source of pressurized air to the motor. The motor drives a spindle 12 inside a motor housing 120 which has external threads 122. Motor housing 120 threadingly engages an attachment 14 which contains internal threads 124. Spindle 12 is rotated by the motor about a longitudinal axis. Connected to attachment 14 is the base 16 of coupling 15 which is threaded onto a threaded neck 18 of attachment 14 by means of threads 20.

Figure 2:
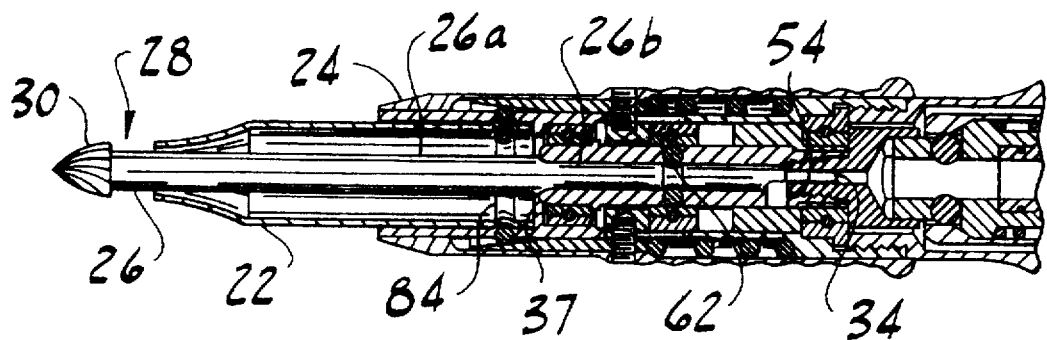
FIG. 2 is a cross-sectional view of the forward end of the surgical instrument with the implement and sleeve installed.

Referring to FIG. 2, support sleeve 22 extends from and is joined at an end 24 of coupling 15 opposite base 16. Guide tube or support sleeve 22 houses cutting implement 28 which has a shank 26. At one end of implement 28 is a cutting element 30. Referring to FIG. 5, implement 28 has a shank diameter of 1/8 inch for the forward portion 26a, beginning at the point where it attaches to cutting element 30. As shown in FIG. 7, the rearward portion 26b of shank 26 is reduced to a 3/32 inch diameter. Referring to FIGS. 6 and 7, two flats or shoulders 37 are located at the junction between forward and rearward portions 26a and 26b. Opposite of cutting element 30 is a tang 34. Tang 34 is a keyed extension from rearward portion 26b. Either shoulders 37 or tang 34 may be used to apply torque to implement 28.

Figure 3:
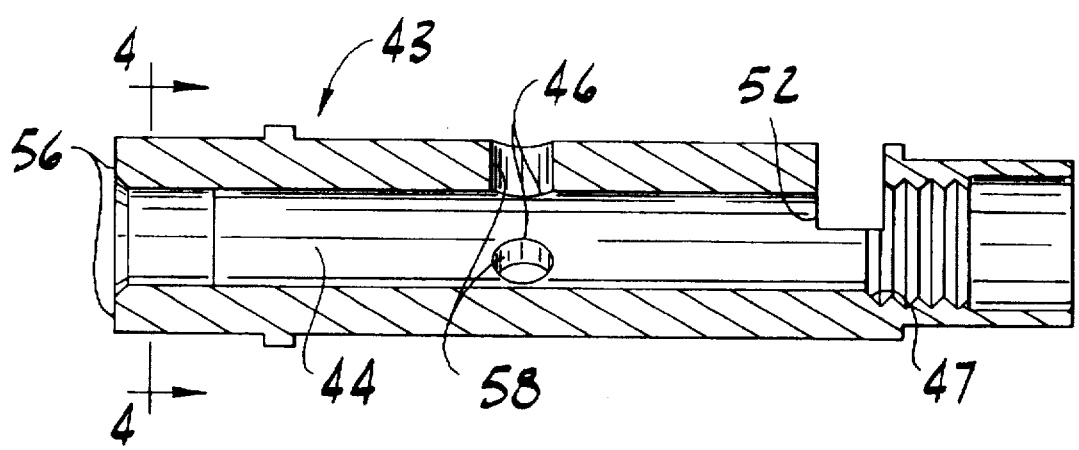
FIG. 3 is an enlarged cross-sectional view of the tubular shaft and is constructed in accordance with the invention.

Referring back to FIG. 1, base 16 contains a cavity 32. The rearward end of a secondary or tubular shaft 43 is contained within cavity 32. Tubular shaft 43 contains internal threads 47 on this end. As shown in FIG. 3, tubular shaft 43 is essentially cylindrical with a central bore 44. Bore 44 closely receives shank rearward portion 26b, but is smaller than forward portion 26a.

An intermediate shaft member or boss 48 is also contained within cavity 32. Boss 48 has a threaded neck 45 which threads into threads 47. Threads 47 and threaded neck 45 are oriented to ensure that they do not become uncoupled during the operation of instrument 10.

Boss 48 has a hexagonally-shaped receptacle 50 for receiving a hexagonally-shaped neck 49 extending from spindle 12 so that boss 48 securely couples to spindle 12. Boss 48 is provided so that tubular shaft 43 can mate with and be driven by spindle 12.

Boss 48 also has an elongated socket 38, which substantially coincides with the axis of implement 28, for receiving tang 34 of implement 28. Socket 38 is formed so that it fits tang 34 in order to transfer torque to implement 28. Tubular shaft 43 contains an inner lock or shoulder 52 upon which shoulder 54 of tang 34 lands and forces the correct orientation of implement 28.

Figure 4:
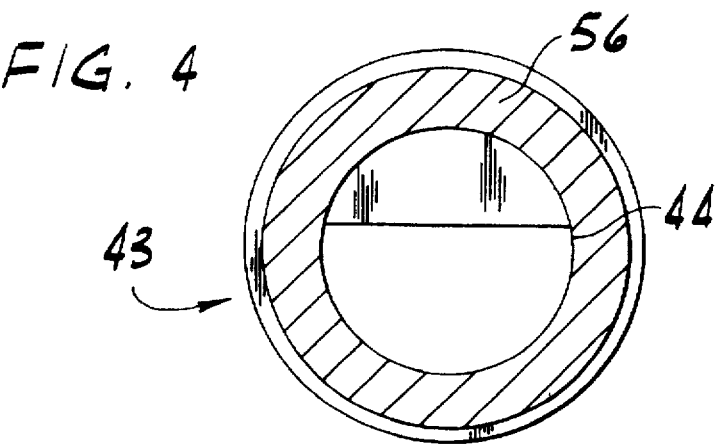
FIG. 4 is an enlarged cross-sectional view of the tubular shaft in FIG. 3 taken along the line 4—4.

Referring to FIGS. 3 and 4, tubular shaft 43 has two shoulders 56 on its forward end. Referring to FIGS. 4 and 6, shoulders 37 of implement 28 engage shoulders 56 when implement 28 is installed. Tubular shaft 43 has a plurality of circular apertures 58 near its axial midpoint which extend radially outward from central bore 44. Each aperture 58 decreases in diameter towards central bore 44 to form a conical locking member seat 46. As shown in FIG. 1, spherical locking members or balls 60 fit within apertures 58 and engage an annular recess 62 in rearward shank portion 26b of implement 28. Prior to the installation of implement 28, balls 60 are free to roll or move within apertures 58, but are prevented from fully entering central bore 44 by locking member seats 46 located at the inner edge of apertures 58. Once implement 28 is installed, balls 60 engage recess 62 and prevent the axial movement of implement 28.

Again referring to FIG. 1, tubular shaft 43 rotates within cavity 32 of base 16 on three roller bearings. A first bearing 70 is located between shoulders 56 and base 16. A second bearing 72 is located between apertures 58 and a boss 74, which slidingly abuts the forward end of base 16. A third bearing 76 is located between base 16 and a boss 78, which abuts the end of tubular shaft 43 that is secured to boss 48. Thus, tubular shaft 43, locking members 60, implement 28, boss 48, boss 78 and the inner races of each bearing all rotate within cavity 32.

Base 16 has two, opposing circular apertures 80 forward of first bearing 70. Spherical locking members or balls 82 fit within apertures 80 and extend into an annular recess 84 on sleeve 22. Balls 82 operate with apertures 80 in exactly the same way as balls 60 operate with apertures 58. Balls 82 prevent the axial movement of sleeve 22 when it is installed in a cavity 86 of coupling 15.

In addition, the first mode comprises a quick release mechanism that can engage and disengage both implement 28 and sleeve 22 simultaneously. Encircling base 16 is a cylindrical collar 90. The lower end of collar 90 closely receives the end of base 16 that connects to attachment 14 so that collar 90 slides along the exterior of base 16 and attachment 14 for a short distance when moved between engaged and disengaged positions along lines parallel to the longitudinal axis of spindle 12. A coiled spring 92 is located between base 16 and collar 90. One end of spring 92 lands on an outer shoulder 94 of base 16, while the other end of spring 92 lands on a rearward end or shoulder 98 of a cam sleeve 96. Cam sleeve 96 is located near first bearing 70 and slidingly receives the forward end of base 16. Spring 92 is axially biased to urge cam sleeve 96 away from shoulder 94. Cam sleeve 96 is attached to collar 90 and boss 74 with screws 98 which extend through holes in each member such that cam sleeve 96, collar 90 and boss 74 move integrally and slidingly together.

Referring to FIG. 8, in a second mode, attachment 14 may be removed from motor housing 120 and replaced by a different attachment 130, which is similar to attachment 14. Spindle 12 is threaded onto a primary shaft 110 which is connected to the motor. Spindle 12 and primary shaft 110 share a central bore 114 for receiving a different tool implement 132 with a shank diameter larger than that of implement 28. Similar to implement 28, tool 132 has an annular recess 134 on its shank 136, a cutting tip 138 on one end, and a tang 140 on the other end that acts as a torque shoulder. Tool 132 is closely received by and fits within bore 114 until tang 140 mates with a receptacle 116 on the rearward end of primary shaft 110. Receptacle 116 acts as a torque shoulder for transferring torque from the motor to the tool.

Spindle 12 has two apertures 120 forward of primary shaft 110. Balls 122 fit within apertures 120 and extend into recess 134 on tool 132 to prevent its axial movement when tool 132 is installed. Balls 122 operate with apertures 120 in exactly the same way as balls 60 operate with apertures 58.

The second mode also comprises a quick release mechanism with a collar 142 that can slidingly engage and disengage both tool 132 and a tool support sleeve 144 simultaneously. This mechanism operates in essentially the same way as the quick release mechanism described for the first mode.

In operation with a first mode, an operator must forcibly slide collar 90 rearward toward spindle 12. This operation moves coupling 15 from the engaged position to the disengaged position. Two events occur simultaneously during this operation. Cam sleeve 96 is tapered on its forward end such that when it moves rearward with collar 90, it permits balls 82 to move freely away from recess 84 of sleeve 22 so that sleeve 22 may be removed. At the same time, second bearing 72 slides rearward, allowing balls 60 to move freely into a small cavity 100 between boss 74 and tubular shaft 43 and away from recess 62 of implement 28 so that implement 28 may be removed. Whenever a surgical implement is to be installed, changed or replaced, collar 90 is moved to the disengaged or retracted position as previously described.

In operation with a second mode, an operator must forcibly slide collar 142 rearward toward spindle 12. This operation permits balls 122 to move freely away from recess 134 of sleeve 22 so that tool 132 may be removed. Tool support sleeve 144 may be removed at the same time as described above in the first mode for sleeve 22. Similarly, whenever a surgical implement is to be installed, changed or replaced, collar 142 is moved to the disengaged or retracted position as previously described.

This invention has several advantages. It allows a conventional rotary machine to drive implements with smaller diameter shafts without additional modification, thereby increasing the versatility of the machine. The invention utilizes a multi-faceted boss that can accommodate various-sized motor spindles to couple with the tubular shaft. The extra set of flats or shoulders on the tubular shaft increases the durability of the implements by providing additional accommodation for torque on the implement. This is especially critical for implements formed from brittle materials such as tungsten carbide. Finally, it is not necessary to remove the base of the surgical instrument in order to access the shaft to remove or replace the implement and sleeve. The quick release coupling device of the invention allows for easy removal, replacement, and conversion between sizes of implements in a much shorter period of time.

While the invention has been shown in only one of its forms, it should be apparent to those skilled in the art that it is not so limited, but is susceptible to various changes without departing from the scope of the invention.

We claim:

1. In a surgical instrument having a rotary motor with an axis of rotation and a motor housing, comprising in combination:

a first resecting tool which is employed in a first mode, the first resecting tool having a shank, a cutting tip, an annular recess on the shank;

a primary shaft secured to and rotated by the motor, the primary shaft having a bore for receiving the shank of the first resecting tool;

a plurality of apertures in the primary shaft;

a ball in each of the apertures of the primary shaft;

an axially moveable primary cam sleeve surrounding the primary shaft for engaging and releasing the balls from the recess in the first resecting tool;

a second resecting tool which is employed in a second mode, the second resecting tool having a shank, a cutting tip, an annular recess on the shank, the shank of the second resecting tool having a different diameter than the shank of the first resecting tool;

a secondary shaft having a rearward end secured to the primary shaft, and a central bore that aligns with the axis for receiving the shank of the second resecting tool;

a plurality of apertures in the secondary shaft;

a ball in each of the apertures of the secondary shaft;

an axially moveable secondary cam sleeve surrounding the secondary shaft for engaging and releasing the balls from the recess in the second resecting tool; and adapter means for releasably securing the secondary shaft to the primary shaft for rotation therewith, so that in the first mode, the secondary shaft is removed from the primary shaft and the shank of the first resecting tool is inserted into the bore of the primary shaft, and in the second mode the secondary shaft is attached to the primary shaft, and the shank of the second resecting tool is inserted into the bore of the secondary shaft.

2. The surgical instrument according to claim 1, wherein the primary and secondary shafts each have a torque shoulder for transmitting torque to the torque shoulder formed on the first and second shanks, respectively.

3. The surgical instrument according to claim 1, wherein the adapter means comprises:

an intermediate member having a rearward end that selectively mates with the primary shaft;

a chuck housing having a rearward end which stationarily couples to the motor housing and a forward end which encloses the secondary shaft; and bearings between the chuck housing and the intermediate member.

4. The surgical instrument according to claim 1, wherein the diameter of the bore of the primary shaft is greater than the diameter of the bore of the secondary shaft.

5. The surgical instrument according to claim 1, wherein the secondary shaft has a plurality of axially spaced apart torque shoulders for transmitting torque to a plurality of axially spaced apart torque shoulders on the second resecting tool.

6. The surgical instrument according to claim 1, wherein the secondary shaft has two torque shoulders, one by flats at the forward end, and one at the rearward end, for transmitting torque to torque shoulders formed on the second resecting tool.

7. The surgical instrument according to claim 1, wherein the adapter means comprises:

an intermediate member having a rearward end that selectively mates with the primary shaft;

a chuck housing having a rearward end which stationarily couples to the motor housing and a forward end which encloses the secondary shaft;

bearings between the chuck housing and the intermediate member;

a secondary release sleeve mated to the chuck housing for axial movement relative to the chuck housing; and means connecting the secondary release sleeve to the secondary cam sleeve so that axial movement of the secondary release sleeve will move the secondary cam sleeve.

8. A surgical instrument for the resection of bone and tissue having a rotary pneumatic motor with a motor housing and a central axis, comprising in combination:

a first resecting tool which is employed in a first mode, the first resecting tool having a shank, a cutting tip, an annular recess on the shank, and a torque shoulder formed on the shank of the first resecting tool for transmitting torque to the cutting tip;

a primary shaft rotated by the motor, the primary shaft having a polygonally-shaped neck and a bore with a forward end that is open for receiving the first tool shank in sliding engagement;

a plurality of apertures in the primary shaft;

a ball in each of the apertures of the primary shaft;

an axially moveable primary cam sleeve surrounding the primary shaft for engaging and disengaging the balls from the recess in the first tool shank;

a second resecting tool which is employed in a second mode, the second resecting tool having a shank with a diameter that is different from the shank of the first resecting tool, a cutting tip, an annular recess on the shank, and a torque shoulder formed on the shank of the second resecting tool for transmitting torque to the cutting tip;

a secondary shaft having a central bore that aligns with the axis, and a forward end that is open for receiving the second tool shank in sliding engagement;

a plurality of apertures in the secondary shaft;

a ball in each of the apertures of the secondary shaft;

an axially moveable secondary cam sleeve surrounding the secondary shaft for engaging and releasing the balls from the recess in the second tool shank;

a chuck housing having a rearward end which stationarily couples to the motor housing and a forward end which encloses the secondary shaft;

bearings between the chuck housing and an intermediate member; and the intermediate member having one end with a polygonally-shaped receptacle that mates with the polygonally-shaped neck on the primary shaft, and another end which secures to a rearward end of the secondary shaft, so that in the first mode, the intermediate member and the secondary shaft are removed from the primary shaft and the shank of the first resecting tool is inserted into the bore of the primary shaft, and in the second mode with the intermediate member and the secondary shaft attached to the primary shaft, the shank of the second resecting tool is inserted into the bore of the secondary shaft.

9. The surgical instrument according to claim 8, further comprising a forward shoulder on the secondary shaft with a flat.

10. The surgical instrument according to claim 8, further comprising:

a forward shoulder on the secondary shaft; and two radially spaced apart flats on the forward shoulder, the flats being parallel to each other and separated by a distance equal to a diameter of the bore.

11. The surgical instrument according to claim 8, further comprising:

a secondary release sleeve mated to the chuck housing for axial movement relative to the chuck housing; and means connecting the secondary release sleeve to the secondary cam sleeve so that axial movement of the secondary release sleeve will move the secondary cam sleeve.

12. The surgical instrument according to claim 8, further comprising:

a guide tube having a bore that aligns with the axis, an annular recess, a rearward end that attaches to the chuck housing, and a forward end that is open for receiving a tool shank;

a plurality of apertures in the chuck housing;

a ball in each of the apertures of the chuck housing; and an axially moveable cam sleeve surrounding the chuck housing for engaging and releasing the balls from the recess in the chuck housing.

13. A surgical instrument for the resection of bone and tissue having a rotary pneumatic motor with a motor housing on a forward end and a central axis, comprising in combination:

a first resecting tool employed in a first mode, the first resecting tool having a shank, a cutting tip, an annular recess on the shank, and a torque shoulder formed on the shank for transmitting torque to the cutting tip;

a primary shaft rotated by the motor, the primary shaft having a polygonally-shaped neck, a bore with a forward end that is open for receiving the first tool shank in sliding engagement, and a torque shoulder for transmitting torque to the torque shoulder formed on the first tool shank;

a plurality of apertures in the primary shaft;

a ball in each of the apertures of the primary shaft;

an axially moveable primary cam sleeve surrounding the primary shaft for engaging and disengaging the balls from the recess in the first tool shank;

a second resecting tool employed in a second mode, the second resecting tool having a shank with a diameter that is different from a diameter of the shank on the first resecting tool, a cutting tip, an annular recess on the shank, and a torque shoulder formed on the shank for transmitting torque to the cutting tip;

a secondary shaft having a central bore that aligns with the axis, a forward end that is open for receiving the second tool shank in sliding engagement, and a torque shoulder for transmitting torque to the torque shoulder formed on the second tool shank;

a plurality of apertures in the secondary shaft;

a ball in each of the apertures of the secondary shaft;

an axially moveable secondary cam sleeve surrounding the secondary shaft for engaging and releasing the balls from the recess in the second tool shank;

an intermediate member having one end with a polygonally-shaped receptacle that mates with the polygonally-shaped neck on the primary shaft, and another end which secures to a rearward end of the secondary shaft;

a chuck housing having a rearward end which stationarily couples to the motor housing and a forward end which encloses the secondary shaft; and bearings between the chuck housing and the intermediate member;

a secondary release sleeve mated to the chuck housing for axial movement relative to the chuck housing; and means connecting the secondary release sleeve to the secondary cam sleeve so that axial movement of the secondary release sleeve will move the secondary cam sleeve.

14. The surgical instrument according to claim 13, further comprising:

a guide tube having a bore that aligns with the axis, an annular recess, a rearward end that attaches to the chuck housing, and a forward end that is open for receiving a tool shank;

a plurality of apertures in the chuck housing;

a ball in each of the apertures of the chuck housing; and an axially moveable cam sleeve within the chuck housing for engaging and releasing the balls from the annular recess in the guide tube.

* * * * *